(12) United States Patent
Ko et al.

(10) Patent No.: US 8,634,924 B1
(45) Date of Patent: Jan. 21, 2014

(54) MEMS IMPLANTED ACOUSTIC SENSOR (75) Inventors: Wen H. Ko, Cleveland Heights, OH (US); Darrin J. Young, Salt Lake City, UT (US); Rui Zhang, Cleveland Heights, OH (US); Ping Huang, Santa Clara, CA (US); Jun Guo, Solon, OH (US); Xuesong Ye, Zhejiang (CN); Cliff A. Megerian, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 485 days.

(21) Appl. No.: 12/782,552

(22) Filed: May 18, 2010

Related U.S. Application Data (60) Provisional application No. 61/179,245, filed on May 18, 2009.

(51) Int. Cl.
*A61N 1/08* (2006.01)
(52) U.S. Cl.
USPC ...... 607/57; 607/3; 607/55; 607/56; 607/115; 607/116; 607/136; 607/137

(58) Field of Classification Search
USPC .............. 607/1–3, 55–57, 115–116, 136–137
See application file for complete search history.

(56) References Cited

U.S. PATENT DOCUMENTS 5,531,787 A * 7/1996 Lesinski et al. ................. 623/10

\* cited by examiner

*Primary Examiner* — Deborah Malamud
(74) *Attorney, Agent, or Firm* — Thompson Hine LLP (57) ABSTRACT

A system and method for a Micro Electro-Mechanical System acoustic sensor, or MEMS acoustic sensor, to be used as an implanted microphone for totally implantable cochlear implants or middle ear implants is presented. The MEMS acoustic sensor comprises a coupler that attaches the sensor to an inner part of the ear, a MEMS acoustic sensor that converts acoustic vibrations into a change in capacitance, and a low-noise interface electronics circuit chip that detects the change in capacitance in the MEMS acoustic sensor, creates an signal representing a portion of the acoustic vibrations, and transmits the signal to one or more other devices, such as a cochlear implant. A method of fabrication enables the MEMS acoustic sensor to be fabricated as a small, less than 1 mm$^3$, light weight, less than 30 mg, device suitable for implantation on a structure of the middle ear.

17 Claims, 11 Drawing Sheets

MEMS IMPLANTED ACOUSTIC SENSOR

CROSS REFERENCE TO RELATED APPLICATIONS

This application claims the benefit of U.S. Provisional Application No. 61/179,245, filed May 18, 2009, entitled "MEMS Implanted Acoustic Sensor", herein incorporated by reference in its entirety.

FIELD

Embodiments of the subject matter described herein relate generally to systems and methods for implantable cochlear or middle ear hearing-aid systems using a Micro Electro-Mechanical System acoustic sensor, or MEMS acoustic sensor.

BACKGROUND

It is estimated one out of ten Americans suffer from conductive as well as sensorineural hearing loss. While conventional hearing aids can offer moderate rehabilitation, inherent limitations, such as ear canal irritations, distortion and occasional ringing, and social problem with being perceived as handicapped have deprived many patients of clear hearing. Partially implantable cochlear and middle ear hearing aid systems can enable people with severe hearing loss to gain improved hearing and speech function. However, the external microphone and electronics present concerns on reliability, comfort, inconvenience, and social stigma.

Implantable microphones can be coupled to middle ear bones. For example, piezoelectric material can be used to sense the malleus vibration. However, piezoelectric material is generally stiff and it is therefore difficult to maintain precise contact with middle ear bones. Electro-magnetic sensors can similarly be mounted on middle ear bones, but present large loading effects that affect sound quality, and have the added disadvantage that they prevent the person from ever getting an MRI. Other microphones are implanted under the skin. However, these microphones tend to pick up body noises, such as chewing, through bone conduction or conduction through body tissues. As a result, most existing semi-implantable middle ear hearing systems and cochlear prosthesis use external microphones.

SUMMARY

Presented is a system and method for a MEMS acoustic sensor for use with implanted hearing systems, such as cochlear implants or middle ear hearing systems, that is suitable for use as an implantable microphone.

In an embodiment, the MEMS acoustic sensor comprises a coupler that attaches to a portion of the middle ear and couples to the MEMS sensor, and an interface communications package for converting the MEMS sensor outputs into a signal that is transmitted to a cochlear implant. In embodiments, the MEMS acoustic sensor communicates with the cochlear implant directly. In embodiments, the MEMS acoustic sensor receives power via a link, such as a direct, capacitive, or electromagnetically coupled link to the implantable hearing systems. In embodiments, the interface communications package is integrated with the MEMS sensor.

By placing the MEMS acoustic sensor within the ear where sound would normally be detected, the MEMS acoustic sensor advantageously takes advantage of the natural directivity of the ear, which naturally focuses sound.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawings in which the reference number first appears.

DETAILED DESCRIPTION

The system and method of the present invention solves the problems associated with hearing assistance devices, namely improving the quality of the sound perceived by the wearer, making the devices cosmetically unobtrusive or less visible to third-parties, and reducing the size, power consumption and coupling issues associated with the devices. Thus, a fully implanted system is envisioned that completely eliminates the need for donning and doffing an external hearing aid or microphone.

In embodiments, the MEMS acoustic sensor is described in relation to a cochlear implant. As is appreciated by those of ordinary skill, the present MEMS acoustic sensor is readily adapted to other implanted hearing systems such as a middle ear hearing implant.

Acoustic Sensor System Architecture

Figure 1A:
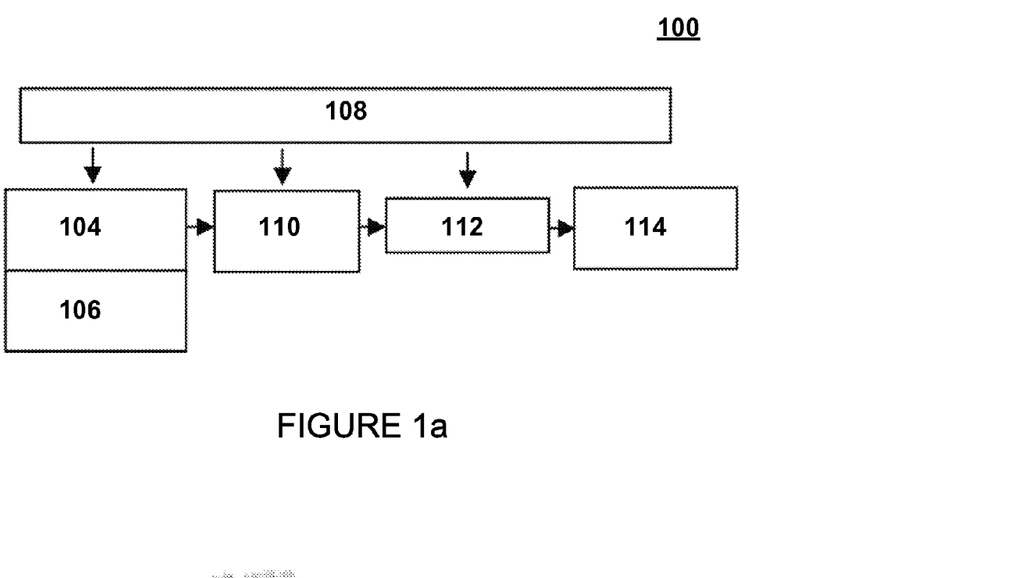
FIG. 1a is a block diagram of an implantable MEMS acoustic sensor and implantable cochlear hearing aid system.
Figure 1B:
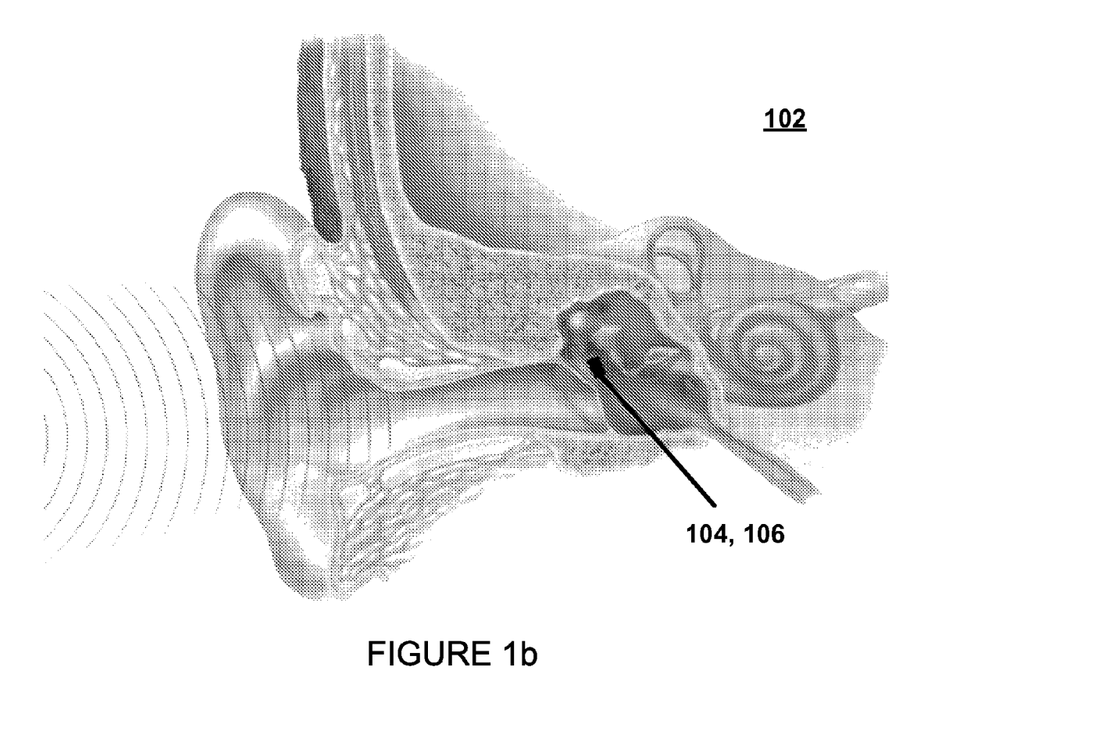
FIG. 1b is an illustration of the implant location of the implantable MEMS acoustic sensor.

Referring now to FIG. 1a, a block diagram of one embodiment of an implantable MEMS acoustic sensor 100 is presented. Referring now also to FIG. 1b, an illustration of the implant location of the implantable MEMS acoustic sensor 100 in the ear 102 when used as an implantable cochlear hearing aid is shown. The MEMS acoustic sensor 100 comprises a displacement sensor 104 that is in electrical communication with an interface electronics package 106. In embodiments, the MEMS acoustic sensor 100 further comprises one or more of the following: a power management and control unit 108, a speech module 110, a stimulator 112, and a cochlear implant 114.

Figure 2:
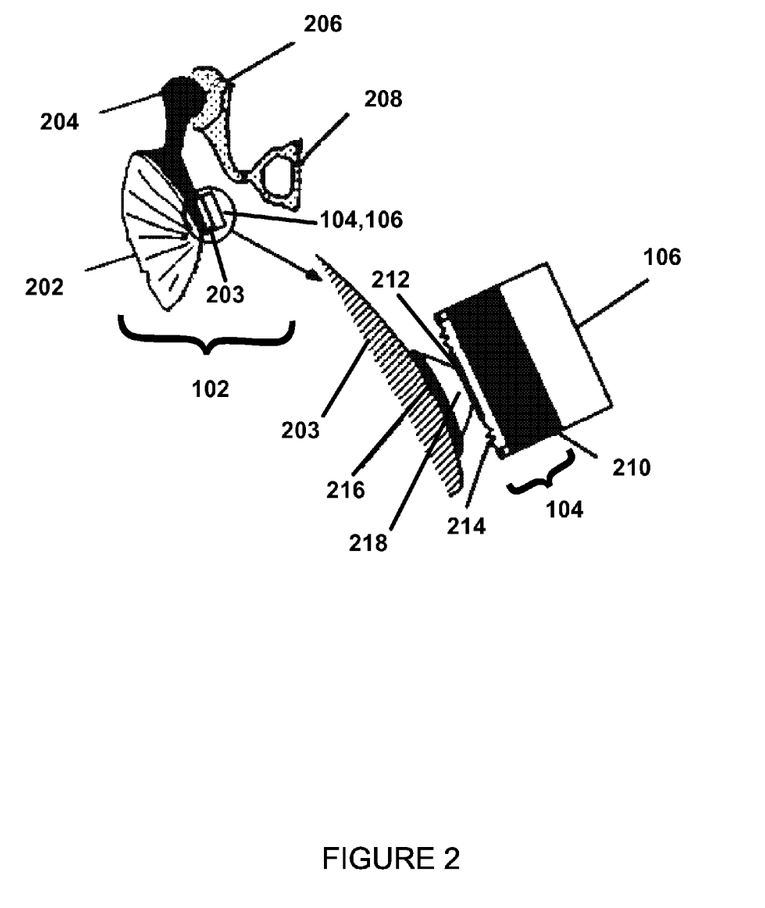
FIG. 2 is a diagram depicting one embodiment of an exemplary MEMS acoustic sensor placed inside the middle ear cavity and mounted on the umbo.

Referring now to FIG. 2, and continuing to refer to FIGS. 1a and 1b, the displacement sensor 104 and interface electronics package 106 are placed inside the middle ear cavity of the ear 102 and coupled to, or mounted on, a structure of the middle ear, for example the diaphragm 202 or umbo 203 as illustrated in FIG. 2, also called the eardrum. Depending upon the specific injury to the person, the displacement sensor 104 could also be mounted on other structures of the ear 102, for example an artificial diaphragm 202 if the person's diaphragm 202 is missing or severely damaged, the malleus 204, the incus 206, or the stapes 208. The displacement sensor 104 detects or measures the changes in the structure of the middle ear due to acoustic vibrations and converts the acoustic vibrations into electronic signals. In an embodiment, the interface electronics package 106 performs signal processing on the electronic signals, for example the interface electronics package 106 may include a speech module 110 to enhance speech, or the interface electronics package may process the electronic signal to reduce noise.

In one embodiment, the output from the MEMS acoustic sensor 100 is used as a microphone output for various implantable hearing aid systems, including a totally implantable cochlear prosthesis system or a totally implantable middle ear hearing systems. In these embodiments, the MEMS acoustic sensor 100 feeds a stimulator 112 that for example may output a stimulus to the stapes 208 or the oval window, also called the vestibular window, respectively, where the stimulus represents the received acoustic signal. It should be noted that the stimulator 112 could also be attached to other parts of the ear 102 including, but not limited to, the malleus 204 and the incus 206, depending upon the actual ear 102 injury to the person. In another embodiment, the MEMS acoustic sensor has an interface communications package that allows it to communicate wirelessly with other devices, either outside the ear, or inside the ear, for example with an implanted cochlear implant 114.

In embodiments, power for the MEMS acoustic sensor 100 is delivered from the implantable hearing systems, which in turn receive power from outside of the ear. In other embodiments, power for the MEMS acoustic sensor 100 is delivered to the MEMS acoustic sensor 100 from a power management and control unit 108. Generally, power is coupled to the devices using magnetic induction or an electromagnetic coupling, although electrically conductive materials such as wires may also be used. Magnetic induction and electromagnetic coupling have the advantage that the power sources can be placed outside the ear, and provide power by bringing them in proximity to the MEMS acoustic sensor 100 without requiring any physical attachment.

Mounting of the MEMS Acoustic Sensor in the Ear

Continuing to refer to FIG. 2, in an embodiment of the MEMS acoustic sensor 100, the displacement sensor 104 comprises a movable silicon diaphragm 212 coupled to a sensor substrate 210 via one or more springs 214. The sensor substrate 210 and silicon diaphragm 212 are capacitively coupled such that movement of silicon diaphragm 212 relative to the sensor substrate 210 can be measured. The interface electronics package 106 is mounted to the displacement sensor 104. The interface electronics package 106 is in electrical communication with the sensor substrate 210 and detects the change in capacitance due to the minute changes in the distance between the sensor substrate 210 and silicon diaphragm 212. The MEMS acoustic sensor 100 is placed inside the middle ear cavity and mounted on the umbo 203 using a coupler 218. The coupler 218 rigidly connects the umbo 203 to the silicon diaphragm 212 of the MEMS acoustic sensor 100.

The coupler 218 also provides a large bonding surface for attaching the MEMS acoustic sensor 100 to the umbo 203. A bonding glue 216 secures the coupler 218 of the MEMS acoustic sensor 100 to the umbo 203. The MEMS acoustic sensor 100 is connected to the umbo 203 using a bio-compatible adhesive. The large bonding surface of the coupler 218 is beneficial because bio-compatible adhesives may not be as strong as other adhesives such as the bonding glue 216. In one embodiment, a dental bonding agent is used, such as that described in Maniglia A J, Nakabayashi N, Paparella M M, Werning J W, "A new adhesive bonding material for the cementation of implantable devices," Otologics surgery. Amer J Otol, vol. 18, pp. 322-327, 1997, which is hereby incorporated by reference.

The coupler 218 uses a strong adhesive, such as epoxy glue or ceramic bonding adhesive, for bonding to the silicon diaphragm 212 of the MEMS acoustic sensor 100, which enables the contacting area of the coupler 218 to be smaller where it attaches to the silicon diaphragm 212. The design of the MEMS acoustic sensor 100 allows the MEMS acoustic sensor 100 to be mounted entirely on the middle ear structure using only a single mechanical connection point. The coupler 218 and silicon diaphragm 212 are the single points of mechanical attachment of the MEMS acoustic sensor 100 to the structures of the ear 102, requiring no other physical attachment to another part of the ear 102. This is advantageous because structures of the ear 102 often move relative to one another, for example when there are changes in air pressure. Hearing aids having multiple points of attachment to the ear 102 often have changes in performance when the structures of the ear 102 move relative to one another.

Characteristics of MEMS Acoustic Sensor and Interface Communications Package

Desired attributes for the MEMS acoustic sensor are detailed as follows:

a) nearly flat frequency response from about 250 to about 8000 Hz;
b) input sound range from 40 to 100 dB SPL;
c) small size and very low power consumption;
d) less than 20 mg mass and force loadings on umbo 203 to limit the loading effect on vibration of the umbo 203; and
e) the ability to withstand large low frequency displacements of the umbo 203 when sudden air pressure changes or large body shocks occur.

During situations when sudden air pressure changes or large body shocks occur, the displacement of the umbo 203 may be up to 10-100 micrometers. Which is 106 times the normal amplitude of the umbo 203 when responding to a small input sound stimulation. Therefore, specially designed sensor and coupling techniques are implemented in the MEMS acoustic sensor 100 to accommodate this large input range.

By mounting the entire MEMS acoustic sensor 100, including displacement sensor 104 and interface electronics package 106 entirely on the umbo 203, the MEMS acoustic sensor 100 responds differently to large low frequency shocks than to small high frequency sounds. The design is based on the reasoning that large body shocks or large air pressure changes, when transmitted to the ear, are large inputs with much lower frequency than the voice or sound signals. The MEMS acoustic sensor 100 thus possesses two nominal operating modes, one responds to low frequency shocks, and the other responds to the sound frequency band.

MEMS Acoustic Sensor and Interface Communications Package

Figure 3:
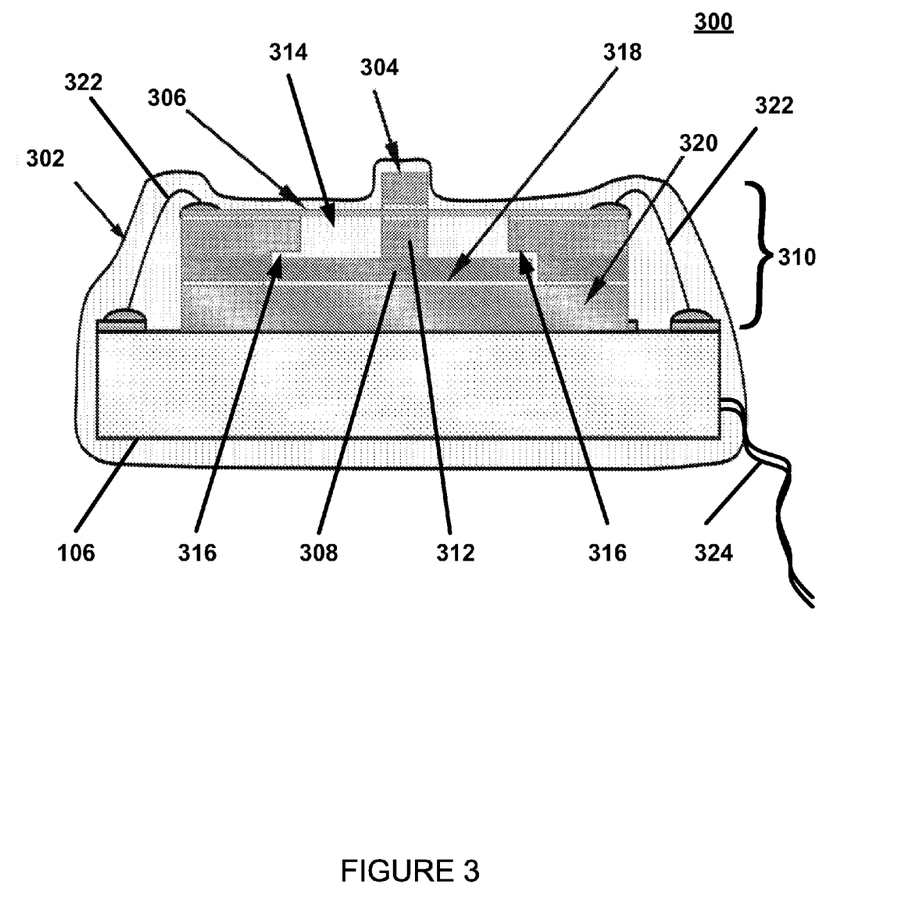
FIG. 3 is a cross-section view of one embodiment of the MEMS acoustic sensor and interface communications package.

Referring now to FIG. 3, a cross-section view of an embodiment of the MEMS acoustic sensor 300 having a sensor module 310 and interface electronics package 106 is presented. An exemplary process flow for fabricating an embodiment of the MEMS acoustic sensor 100 is presented in FIGS. 10a-f and the accompanying detailed description below. The MEMS acoustic sensor 300 is small, weighing less than 30 mg or even 20 mg and having a size of about 1 mm$^3$. The MEMS acoustic sensor 300 is enveloped in a biocompatible material coating 302, such as a protective epoxy, to prevent contamination of MEMS acoustic sensor 300 components from body fluids and prevent any reaction to the MEMS acoustic sensor 300 by the body. The small size and weight of the MEMS acoustic sensor 300 allow the MEMS acoustic sensor to be placed on structures of the middle ear 102 including but not limited to the umbo 203, the malleus 204, the incus 206, or the stapes 208.

The MEMS acoustic sensor 300 enables separation of responses to low frequency shock and to high frequency sound signals. The sensor module 310 comprises a sensor handle 304 that attaches to a top plate 306. The sensor handle 304 is created on the top plate 306 during fabrication and attaches to the coupler 218 (not shown) for attachment to the umbo 203 (also not shown.) The top plate 306 is a flexible member that displaces when pressure is applied to the sensor handle 304 due to vibrations of the umbo 203. The top plate 306 also provides a seal for the chamber 314. Movement of the top plate 306 is transferred to the sensor electrode 308 through a displacement coupler 312. The displacement coupler 312 permits the sensor electrode 308 to be positioned within a chamber 314 below a displacement stop 316. The displacement stop 316 limits the displacement of the sensor electrode 308 and top plate 306 caused by shock or loud sounds that could otherwise damage the top plate 306 and sensor electrode 308.

A gap 318 between the sensor electrode 308 and sensor substrate 320 allows the sensor electrode 308 and sensor substrate 320 to function as a variable capacitor, the capacitance of which changes as the sensor electrode 308 moves relative to the sensor substrate 320. A bonding wire 322 is electrically connected to the top plate 306, which is capacitively couple to the displacement coupler 312 and sensor electrode 308. The bonding wire 322 electrically connects to electric contacts 302 on the interface electronics package 106. In an embodiment, the sensor substrate 320 is in electrical contact with the interface electronics package 106. In embodiments, the sensor substrate 320 and sensor electrode 308 are in electrical communication with the interface electronics package 106 by direct contact, by a connecting wire 324, an electrode, one or more bonding wires 322, or any other electrical or electromagnetic means as would be understood in the art. In embodiments, the interface electronics package 106 of the MEMS acoustic sensor 300 is connected to an external device such as a cochlear implant 114, a stimulator 112, or a middle ear hearing system using connecting wires such as connecting wire 324, which can include multiple wires, optical interfaces, or other communication or power capabilities. In embodiments, the interface electronics package 106 communicates with an external device electromagnetically.

Model of MEMS Acoustic Sensor and Response

Figure 4:
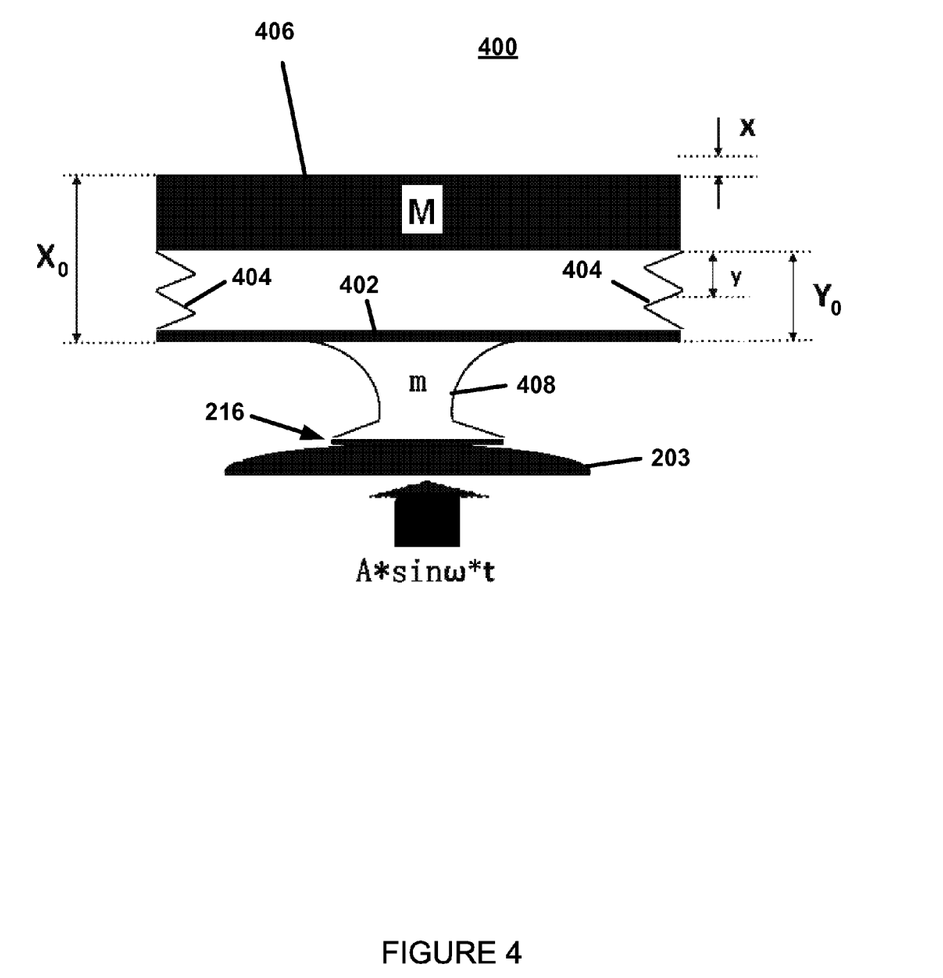
FIG. 4 is a diagram depicting a model of an embodiment of the MEMS acoustic sensor.

Referring now to FIG. 4, a schematic model of sensor unit 400 is presented. The capacitive sensor electrode, or diaphragm 402, and the mounting stub 408 have a mass, m. The diaphragm 402 is connected to a set of springs 404, S, with negligible mass and a total stiffness, k. The other end of the springs 404 are connected to a base, or substrate 406, with a mass M, and M>>m. In one embodiment, the sensor unit 400 has a total mass, (M+m), less than 20 mg. In another embodiment, the sensor unit 400 has a total mass (M+m) less than 30 mg. The capacitance measured between the diaphragm 402 and the base, or substrate 406, represents the displacement of the sensor unit 400.

The stiffness and masses of the various elements of the sensor unit 400 presented in FIG. 4 modulate the capacitive response of the sensor unit 400 as a function of input frequency. For low frequency (e.g. <200 Hz) vibrations, the sensor unit 400 mass (M+m) would move with the input displacement, resulting in small sensor output. For large amplitude low frequency shocks, the sensor unit 400, (M+m), would move with the umbo 203 but the total loading on the umbo 203 would be limited to the mass (M+m). When the input is in the sound frequency (500 Hz-8 kHz) range, the substrate 406, M, would be nearly stand-still, and the diaphragm 402, m, would respond to the vibrations by converting the vibrations into capacitance changes. An amplifier circuit of the interface electronics package 106 (not shown) then converts the capacitance changes into electrical signals, resulting in the acoustic sound voltage output.

The sensor unit 400 receives the driving displacement from umbo 203 through the mounting stub 408 to the diaphragm 402, m. The substrate 406, M is coupled to the diaphragm 402 and mounting stub 408, m through a spring 404, S with a combined spring constant, k. The capacitance, C, between the m and base M is the acoustic sensor. The initial positions of $X_0$, and $Y_0$ of the substrate 406 and diaphragm 402 respectively include the effects of Earth's gravitational force, g, and are assumed to be constant.

When the input displacement A*sin ω*t is applied, assuming the displacement of M is x; the length change of the spring is y; the total damping is b; and x, y, and b are functions of frequency and time. The system response can be described by the following force equations:

$$F_{spring} = ky = k(A * \sin\omega * t - x) \quad (1)$$

$$M\frac{d^2x}{dt^2} + b\frac{dx}{dt} - k(A * \sin\omega * t - x) = 0 \quad (2)$$

$$k * A * \sin(\omega * t) = M\frac{d^2x}{dt^2} + b\frac{dx}{dt} + kx \quad (3)$$

The solution of Laplace Transform of equation (3) for x/A* is:

$$H(j\omega) = \frac{x}{A^*} = \frac{\frac{k}{M}}{(j\omega)^2 + \frac{b}{M}j\omega + \frac{k}{M}} \quad (4)$$

The system characteristics are determined by two factors, the first critical frequency $\omega_c = 2\pi F_c$ and system damping ratio ζ, where $$\zeta = \frac{b}{2\sqrt{kM}} \Rightarrow b = 2\zeta\sqrt{kM} \quad (5)$$

For hearing applications, the phase variation is not important. The sensor unit 400 is a heavily damped device.

Figure 5:
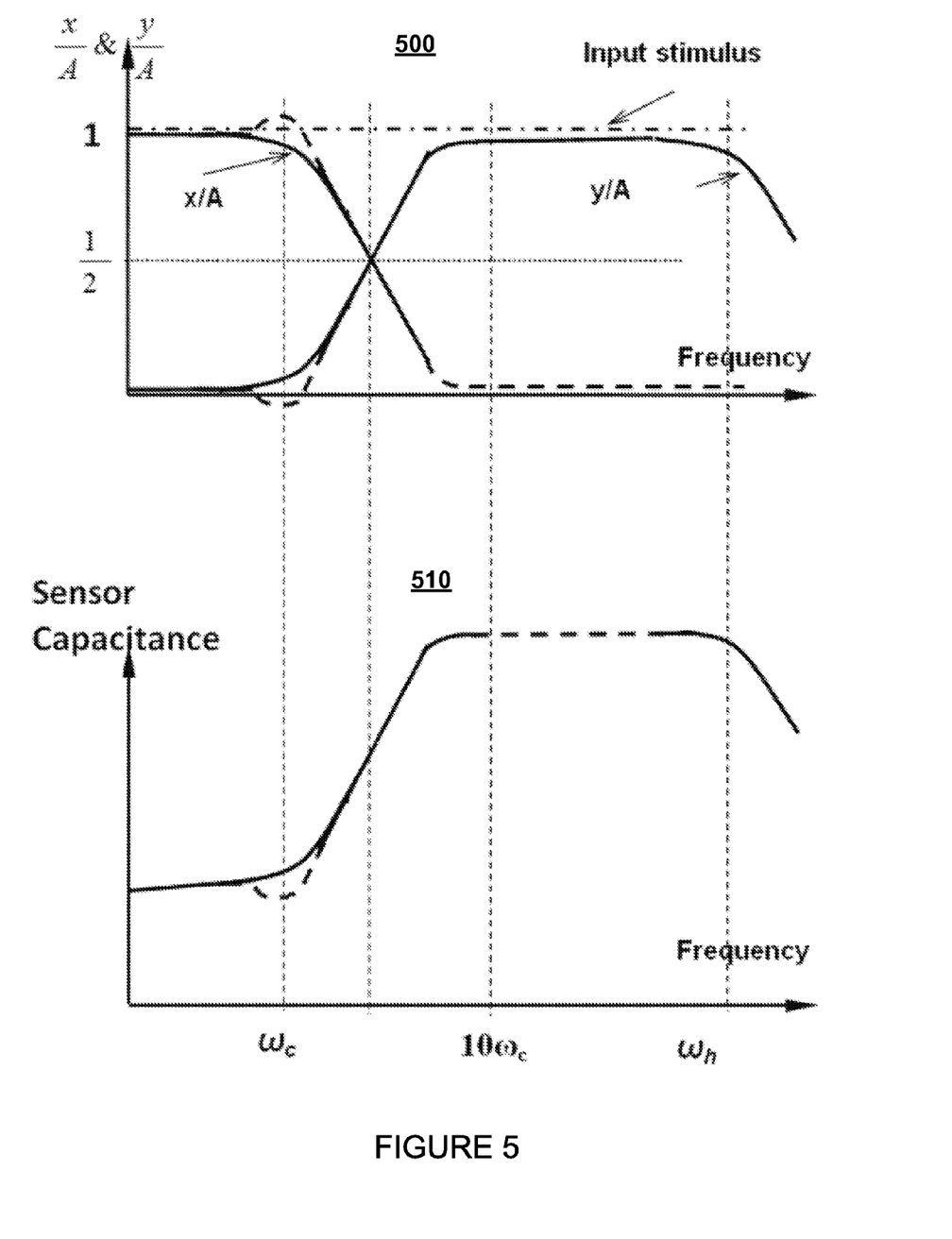
FIG. 5 is a set of graphs depicting the theoretical frequency response and sensor capacitance of the MEMS acoustic sensor of FIG. 4.

Referring now to FIG. 5, a frequency response graph 500 and a sensor capacitance 510 graph are presented. In the frequency response graph 500, the x and y amplitudes responding to the input A* depend on the value of ζ and are plotted. The best damped response occurs where ζ is equal to $1/\sqrt{2}$, as ω approaches zero, x/A* approaches one, and y/A* approach zero. For ζ=1/√2 and ζ<1/√2 (under-damped) cases, the x and y responses are also shown.

In the sensor capacitance 510 graph, the capacitance response to A* (and y) is shown. The capacitance of a parallel plate capacitor, neglecting the fringe effect, is:

$$C = S\varepsilon/Y = (S\varepsilon/Y_o + \Delta C) \quad (6)$$

where C, S, $\varepsilon$ and $Y_o$ denote the capacitance, electrode area, dielectric constant, and separation between the electrodes, respectively. The amplitude of capacitance change due to input A* and change of spring length, y, is:

$$\Delta C = -(S\varepsilon/Y_o^2)y \quad (7)$$

where $Y_0$ corresponds to the initial length of the spring. The length change y is a function of K of the spring and M.

Assuming the umbo 203 has large driving capability, the input displacement A* would be equal to vibration of the umbo 203, and the sensor unit 400 would be a true displacement sensor. The frequency $\omega_c = 2\pi F_c = (k/M)1/2$ can be designed to be below 200 Hz. As frequency increases beyond the sound frequency band, the force loading of "m" on the umbo 203 increases with $\omega^2$. The increased force loading effect at high frequencies cannot be neglected. Beyond a frequency $\omega_h$, the sensor unit 400 sensitivity drops off.

Fabricated MEMS Acoustic Sensor

Figure 6:
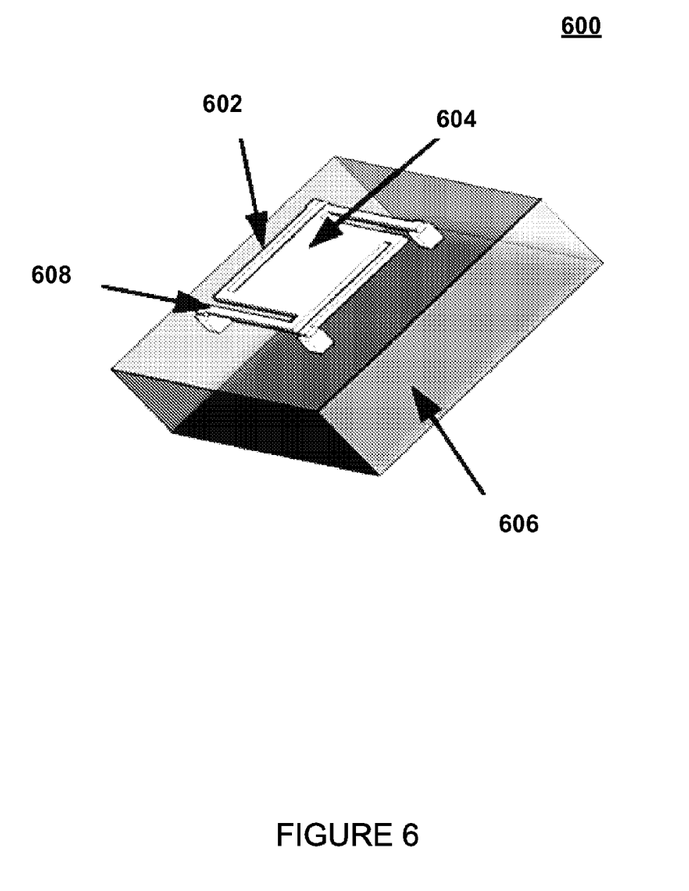
FIG. 6 is a diagram depicting a fabricated MEMS acoustic sensor highlighting the spring structures for adapting the spring constant between the diaphragm and sensor substrate.

Referring now to FIG. 6, one embodiment of a MEMS acoustic sensor 600 is illustrated. The exemplary MEMS acoustic sensor 600 has a mass (M+m) of 20 milligrams, and $\omega_c = 2\pi F_c$, where $F_c = 200$ Hz, and a spring constant K of approximately 31.2N/m. There are four folded cantilever-beams 602 that act as flexible members to support the diaphragm 604 while allowing it to move. The diaphragm 604 functions as one electrode of a capacitor in conjunction with the substrate 606 which functions as the complementary electrode of the capacitor. The cantilever-beams 602 are secured to the substrate 606 by anchor structures 608. The cantilever-beams 602 act as the springs in the system, the K value of each cantilever-beams 602 being approximately 7.8N/m. For a given spring constant, the dimension of the cantilever-beam 602 springs can be calculated from the equation below:

$$K = \frac{EBh^3}{4L^3} \quad (8)$$

where, h, L, B are the thickness, length, and width of the spring; and E is the Young's modulus.

These calculations are used to size a MEMS acoustic sensor 600. In one embodiment a MEMS acoustic sensor 600 is fabricated on a 2×2 mm silicon chip substrate 606. The calculated silicon cantilever-beam 602 dimensions, with 200 Hz critical frequency and 20 μm thickness, is approximately 80 um in width and approximately 1454 um in length. However, the spring in the exemplary fabricated MEMS acoustic sensor 600 has a length of 850 um, due to compromises on silicon chip size and layout constrains from the shared MOSIS fabrication processes on SOI (Silicon on Insulator) wafer. Due to such constraints, the fabricated springs are shorter than designed. For a spring with M=20 mg, L=850 μm, B=80 μm, and h=20 μm the calculated Fc1 is 445 Hz. The exemplary MEMS acoustic sensor 600 weighs about 25 mg and the SOI wafer used also has a 2 μm silicon dioxide on the top of the 20 μm device layer. If the difference in Young modulus of silicon and Silicon dioxide is neglected, the recalculated Fc is 459 Hz. The measured Fc on prototype MEMS acoustic sensor 600 is about 480 Hz. This 4.5% increase in Fc may be contributed to the normal dimensional variation in MOSIS fabrication processes.

Interface Communications Package

Figure 7:
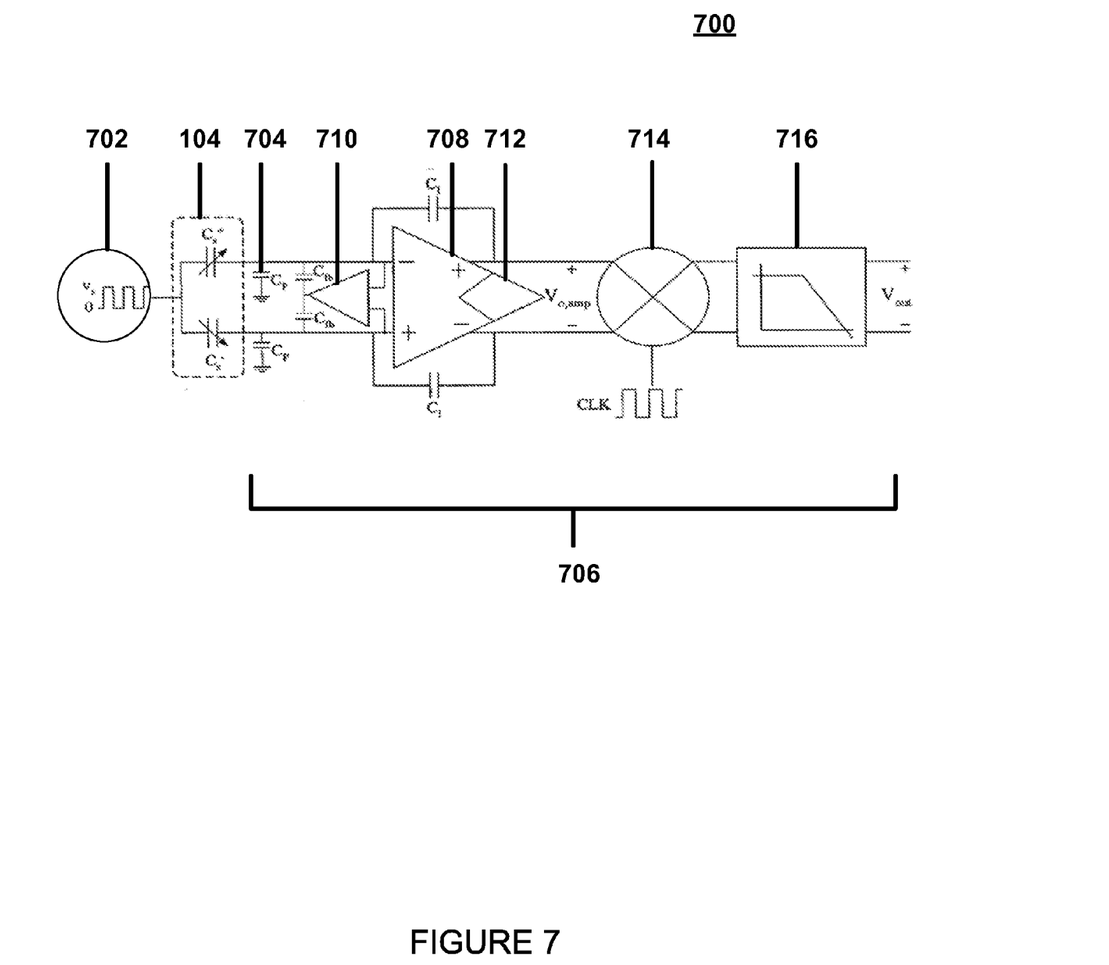
FIG. 7 is a schematic of an exemplary capacitive sensor interface electronics architecture.

Referring now to FIG. 7, a schematic of an exemplary capacitive sensor interface architecture 700 for the interface electronics package 106 is illustrated. The interface electronics package 106 is electrically connected to the displacement sensor 104. The output of the capacitive sensor interface 706 is correlated with capacitance change, AC. The capacitive sensor interface 706 functions as a capacitance to voltage converter, converting AC into a voltage, and as an amplifier. In an embodiment, the output of the capacitive sensor interface 706 represents the output of an implantable microphone. In an embodiment, the illustrated capacitive sensor interface architecture represents only a portion of the interface electronics package 106 used to convert the input from the displacement sensor 104 into a usable output, which is then further processed by signal processing methods known in the art, including, but not limited to, analog signal processing and digital signal processing.

In an embodiment, the MEMS acoustic sensor 100, 300, 600 is an integrated module and includes the MEMS sensor, the mounting, and the interface electronics package 106. The sensitivity of the displacement sensor 104 is limited by the total noise of the entire MEMS acoustic sensor 100, 300, 600. The capacitive portion of the displacement sensor 104 itself has very low noise and consumes no real average power. To satisfy the system sensitivity, the capacitive sensor interface 706 comprises a low noise interface circuit. The circuit noise is usually specified by the input-referred noise power spectral density.

The capacitive sensor interface 706 is designed as a low noise, high performance, capacitive strain sensor circuit. This allows the capacitive sensor interface 706 to measure the change in capacitance of the displacement sensor which can be as small as 0.01 pF The circuit of the capacitive sensor interface 706 has a resolution in capacitance change of 250 pF over DC-10 kHz bandwidth and an input-referred voltage noise power spectral density of 5V/√Hz. The displacement sensor 104 and a fixed capacitor 704 are used as the differential input capacitances. They are driven by a 1 MHz clock signal 702 with 3 Vs amplitude and are interfaced by a differential charge amplifier 708, which converts the sensor capacitance-change to an output voltage signal. The high clock frequency for the clock signal 702 is chosen to modulate the sensor information away from the low frequency noise, such as 1/f noise, of the differential charge amplifier 708 as a means to achieve high sensitivity. An input common-mode feedback (ICMFB) circuit 710 and an output common-mode feedback (OCMFB) circuit 712 are incorporated with the differential charge amplifier 708 to minimize its common-mode shift caused by a drifting clock signal 702 thereby suppressing any offset signal due to the parasitic capacitance mismatch and drift over time. The output of the differential charge amplifier 708 is then mixed in a mixer 714 using the same clock signal to remove, or demodulate, the clock signal, and then low-pass filtered using a low pass filter 716 to obtain an output voltage, $V_{out}$, which represents the desired sensor information, for example an audio signal. In one embodiment, the capacitive sensor interface 706 circuit consumes 1.5 mA at 3 volts. Further details of a low noise capacitance to voltage converter is provided in M. Suster, N. Chaimanonart, J. Guo, W. H. Ko, and D. Young, "Remote-Powered High-Performance Strain Sensing Microsystem," Techn. Dig., IEEE Int. Conf. on MEMS, Miami, Fla., pp. 255-258, 2005", herein incorporated by reference in its entirety.

MEMS Acoustic Sensor Actual Response

Figure 8:
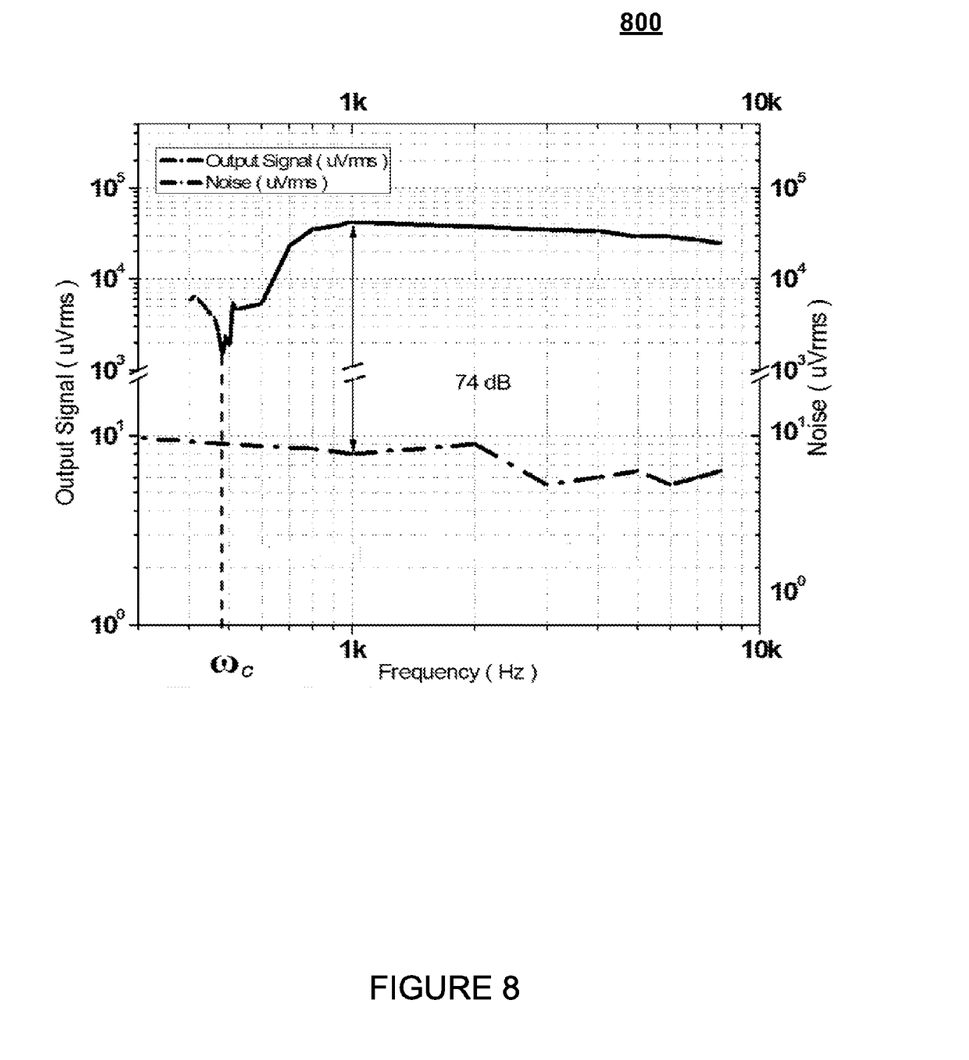
FIG. 8 is a graph of the frequency response of the fabricated MEMS acoustic sensor of FIG. 6.

Referring now to FIG. 8, a frequency response graph 800 of the frequency response (y/A*) of one embodiment of the MEMS acoustic sensor 600 is presented. An exemplary MEMS acoustic sensor 600 was tested with simulation unit at the set amplitude equivalent to a sound input of 97 dB SPL @1 kHz. The frequency response graph 800 illustrates the measured voltage outputs as well as the system noise as functions of frequency. The exemplary MEMS acoustic sensor 600 has a critical frequency, $\omega_c$, around 480 Hz. Increasing the weight of the MEMS acoustic sensor 600 from 25 mg to 125 mg shifted the cutoff frequency from 480 Hz to below 200 Hz, while maintaining near flat frequency response from 800 to 8 kHz with variation of less than 6 dB. This illustrates that $\omega_c$ of the MEMS acoustic sensor 600 can be designed as per equation (6). For a MEMS acoustic sensor 600 with 30 mg mass, the signal to noise voltage ratio (signal analyzer bandwidth is 50 Hz) is 74 dB, at 1 kHz and 97 dB SPL input. This indicates a signal noise ratio of 71 dB is achieved if the interested signal bandwidth is 100 Hz. Therefore, a minimum detectable input sound level (with 3 dB SNR) of 29 dB SPL can be achieved around 1 KHz with 100 Hz channel bandwidth.

Figure 9:
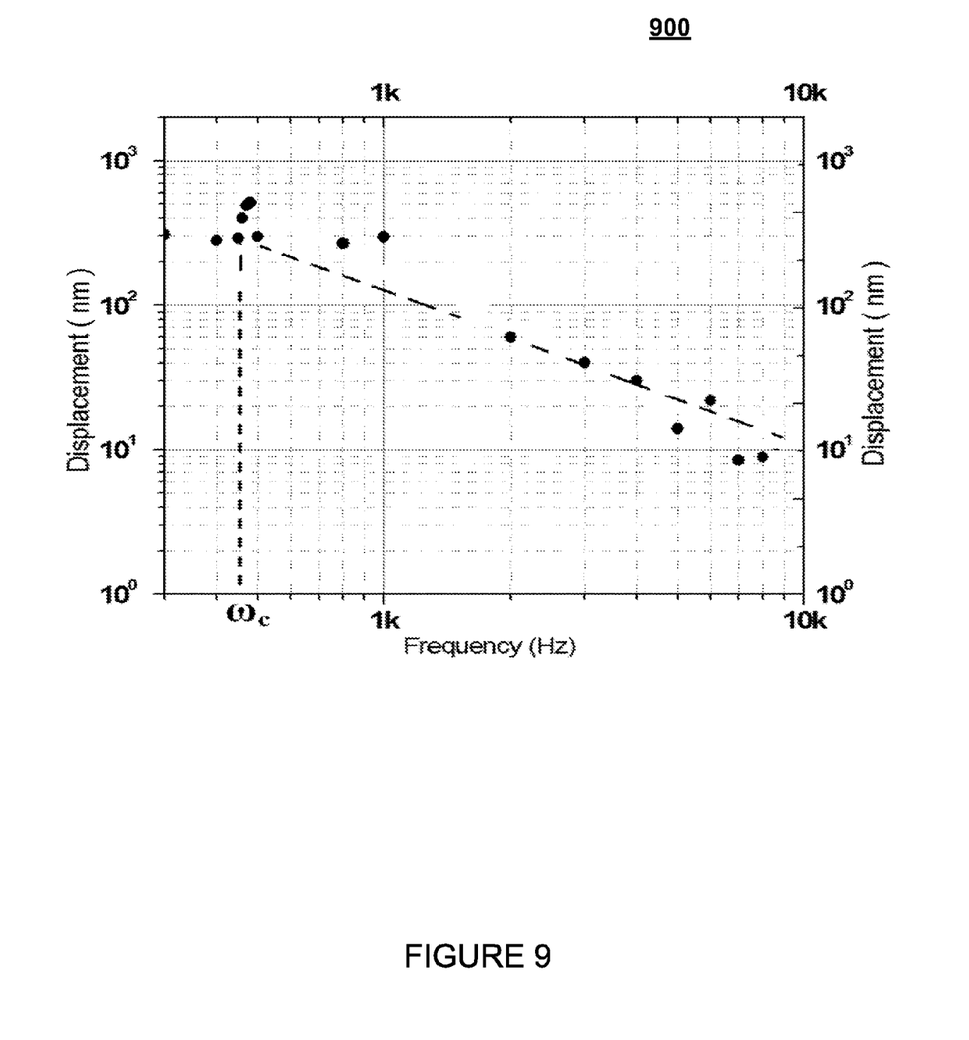
FIG. 9 is a graph of the displacement of the substrate of the MEMS acoustic sensor of FIG. 6 when under test.

FIG. 9 is a displacement graph 900 of the displacement (x/A*) of the substrate 606 of a MEMS acoustic sensor 600, where the response below or near the critical frequency, $\omega_c$ and the decrease in amplitude beyond $\omega_c$ are clearly illustrated as predicted in the graphs 500, 510 of FIG. 5. The displacement graph illustrates that for high amplitude low frequency sounds below or near $\omega_c$, which is approximately between 200 and 500 Hz, such as shocks or abrupt loud noises, the substrate 606 of the MEMS acoustic sensor 600 responds favorably by moving with the umbo 203, which not only helps the sensitive microphone structures of the MEMS acoustic sensor 600 from being structurally damaged by loud sounds or shocks but also results in favorable recovery time after loud sounds and shocks. This is unlike most other hearing aids which tend to recover slowly and typically cause the user to experience a period of muting or quiet after a shock or loud sound is experienced. Further, for sounds in the higher frequency range of speech, the spring-like cantilever-beams 602 in the MEMS acoustic sensor 600 allow the substrate 606 to move relative to the umbo 203 thereby producing the change in capacitance as described above for sounds in the frequency range of speech. The MEMS acoustic sensor 600 can therefore withstand large shocks of approximately $10^6$ times the normal acoustic sound level while retaining high sensitivity and wide bandwidth.

Process Flow Diagram Detailing the Process for Creating the MEMS Acoustic Sensor Referring now to FIGS. 10a-e, a series of diagrams illustrate one embodiment of the process flow for creating a MEMS acoustic sensor 600. The MEMS acoustic sensor 600 for middle ear sound sensing in one embodiment is fabricated using a micro-machining fabrication process depicted in FIGS. 10a-e which illustrate the major fabrication steps of one exemplary process. As known to those of ordinary skill in the art, the specified structural measurements vary according to fabrication steps, equipment, and design options and measurements are provided to enable a person of ordinary skill in the art to understand the fabrication process.

Figure 10A:
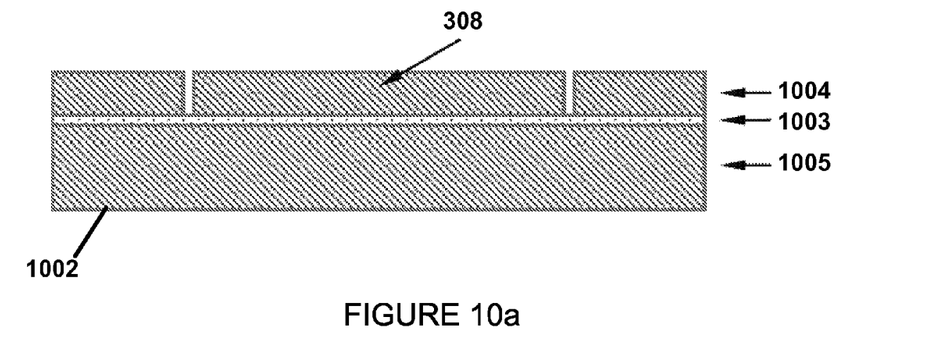
FIGS. 10a-e are process flow diagrams detailing an embodiment of a process for creating a MEMS acoustic sensor.

The process begins with a commercial 4-inch diameter silicon-on-insulator (SOI) wafer 1002 comprising a silicon substrate 1005, a silicon oxide ($SiO_2$) isolation layer 1003, and a 30-μm thick silicon structure 1004 which serves as the sensor electrode 308 structure later. The wafer 1002 starts with the standard photolithography process, followed by a deep reaction ion etch (DRIE) to generate the sensor electrode 308 structure, as shown in FIG. 10a.

Figure 10B:
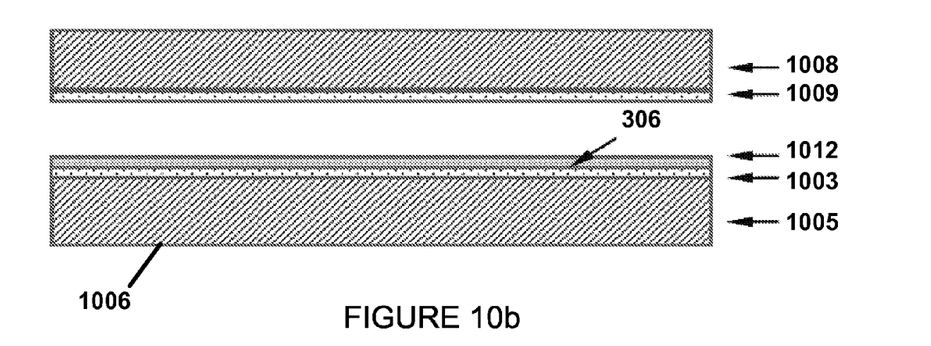
Figure 10C:
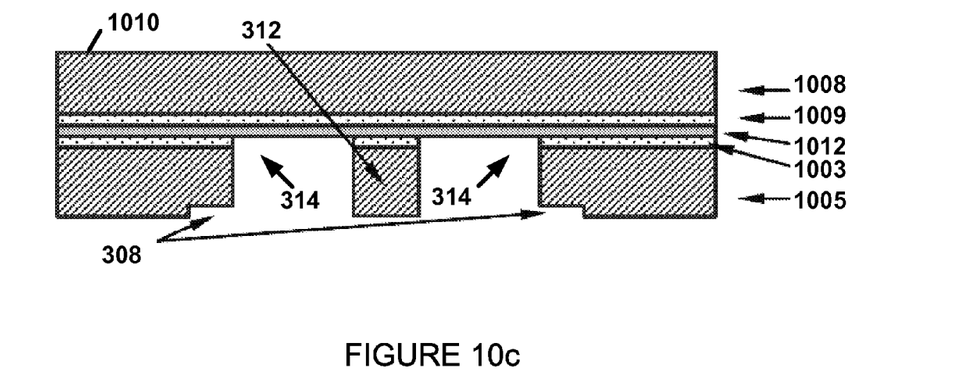

The second wafer 1010 is a special 5-layer wafer, fabricated by fusion bonding a SOI wafer 1006 comprising a silicon substrate 1005, a silicon oxide ($SiO_2$) isolation layer 1003, and a 5-μm silicon layer 1012 that serves as the top plate 306, to a bare silicon wafer 1008 coated with 1.5-gm thermal grown silicon oxide ($SiO_2$) layer 1009, as shown in 10b. The wafer 1010 under goes two etch processes to generate a depression that becomes the displacement stop 316 structure, another depression that becomes the chamber 314, and the displacement coupler 312 structure, as shown in FIG. 10c.

Figure 10D:
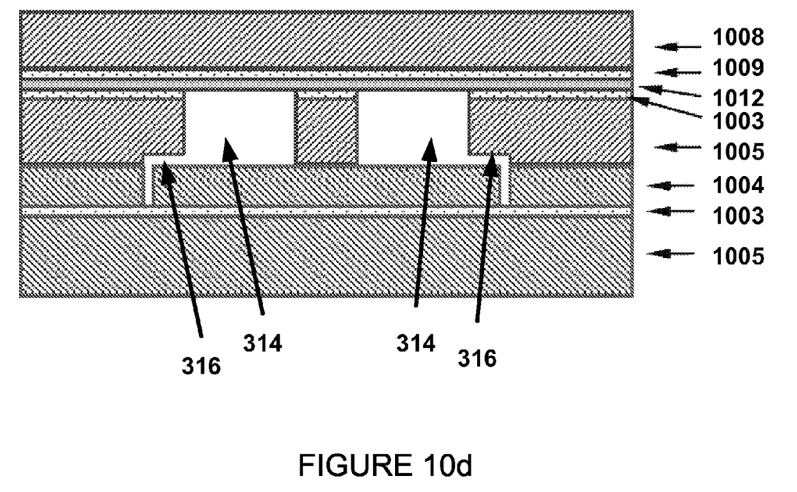
Figure 10E:
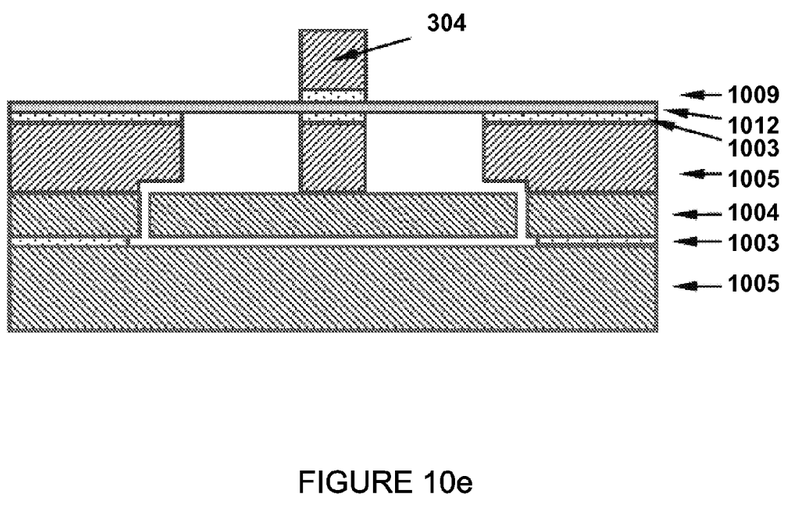

Then the two wafers 1002, 1010 are bonded together using a fusion bonding technique as shown in FIG. 10d. The bonding creates the chamber 314 and affixes the displacement coupler 312 to the sensor electrode 308. Another etching process generates the sensor handle 304 structure, that is adapted to be affixed to the umbo 203 in the final application in the ear 102 using an epoxy glue or ceramic bonding adhesive as discussed above, shown in FIG. 10e. The top plate 306 structure is released by etching away the underneath sacrificial silicon oxide layer 1009 using HF vapor release process. Electrical connections are made between the displacement sensor 104 and the interface electronics package 106, or interface electronics substrate, and the displacement sensor 104 is bonded to the interface electronics package 106 to form a single unit suitable for encapsulation as shown in FIG. 3.

The micro-fabricated MEMS acoustic sensor 300 is a totally silicon-sealed structure with the movable parts protected by the displacement stops 316. Therefore the MEMS acoustic sensor 300 can stand high vibration introduced by human body during sports or other events. In embodiments, a bio-compatible material coating 302, such as a protective epoxy, is applied to achieve the device bio-compatibility.

While various embodiments of a system and method for a MEMS acoustic sensor have been described above, it should be understood that they have been presented by the way of example only, and not limitation. It will be understood by those skilled in the art that various changes in form and details may be made therein without departing from the spirit and scope of the invention as defined. Thus, the breadth and scope of the present invention should not be limited by any of the above-described exemplary embodiments.

We claim:

1. A sensor system, comprising:
   microelectromechanical sensor (MEMS sensor) having at least a movable diaphragm, wherein said MEMS sensor converts a vibration of a middle ear structure into a change in capacitance of said MEMS sensor when an acoustic vibration is present;
   a coupler having a first end connected to said movable diaphragm and a second end for attaching said MEMS sensor to said middle ear structure, and
   an interface electronics package in communication with said MEMS sensor, adapted to detect said change in capacitance of said MEMS sensor and convert said change in capacitance into a signal representing at least a portion of said acoustic vibration.

2. The sensor system of claim 1, wherein said middle ear structure is selected from the group consisting of an eardrum, an umbo, a malleus, an incus, a stapes, and a vestibular window.

3. The sensor system of claim 1, wherein said interface electronics package is low noise interface electronics package.

4. The sensor system of claim 1, wherein said interface electronics package further comprises:

clock signal source for providing a clock signal to said MEMS sensor;

a reference capacitor that receives said clock signal;

a differential charge amplifier that receives an output from said reference capacitor and an output from said MEMS sensor, said differential charge amplifier converting a change in capacitance of said MEMS sensor into an voltage signal;

a mixer for receiving said voltage signal from said differential charge amplifier and removing frequency components in said voltage signal relating to said clock signal to producing a demodulated signal; and a low pass filter for receiving said demodulated signal and producing said electrical signal representing a portion of said acoustic vibration.

5. The sensor system of claim 4, wherein said differential charge amplifier further comprises:

an input common-mode feedback (ICMFB) circuit; and an output common-mode feedback (OCMFB) circuit, wherein said ICMFB and said OCMFB minimize common-mode shift caused by a drift in said clock signal, and suppress an offset signal due to said drift and a parasitic capacitance mismatch.

6. The sensor system of claim 5, wherein said electrical signal representing said portion of said acoustic vibration has a frequency range of about 250 Hz to about 8000 Hz.

7. The sensor system of claim 1, wherein said MEMS sensor is a capacitive displacement sensor.

8. The sensor system of claim 1, wherein said MEMS sensor is a silicon based capacitive displacement sensor that weighs less than 30 mg and is less than 1 mm$^3$ in dimension.

9. The sensor system of claim 1, said MEMS sensor further comprising:

a base;

a flexible member, wherein said movable diaphragm is in communication with said base through said flexible member; and a displacement stop incorporated into said base to limit displacement of the movable diaphragm relative to said base, wherein said base and said movable diaphragm form a capacitor whose capacitance is dependent upon a gap between said base and said movable diaphragm.

10. The sensor system of claim 1, wherein said first end of said coupler has a first contacting area and said second end of said coupler has a second contacting area that is greater than said first contacting area.

11. The sensor system of claim 1, wherein said interface electronics package communicates said signal to an implant stimulator of a totally implantable hearing system.

12. The sensor system of claim 1, wherein said interface electronics package communicates said signal electrically to a cochlear implant.

13. The sensor system of claim 1, wherein said interface electronics package is adapted to communicate said signal to a cochlear implant electromagnetically.

14. A microelectromechanical sensor (MEMS sensor) for attaching to a structure of a middle ear, comprising:

a base;

a movable diaphragm in communication with said base through a flexible member, said base and said movable diaphragm forming a capacitor whose capacitance is dependent upon a gap between said base and said movable diaphragm, and wherein a width of said gap changes when an acoustic vibration is present in the middle ear;

a displacement stop incorporated into said base to limit displacement of the movable diaphragm relative to said base; and a coupler having a first end connected to said movable diaphragm and a second end for attaching the MEMS sensor to the structure of the middle ear.

15. The MEMS sensor of claim 14, wherein said first end of said coupler has a first contacting area and said second end of said coupler has a second contacting area, and wherein said first contacting area is less than said second contacting area.

16. The MEMS sensor of claim 14, wherein the coupler attaches the MEMS sensor to a part of the middle ear selected from the group consisting of an eardrum, an umbo, a malleus, an incus, a stapes, and a vestibular window.

17. The MEMS sensor of claim 14, further comprising:

an interface electronics package adapted to detect a change in a capacitance of said MEMS sensor and to convert said change in said capacitance into an signal representing a portion of said acoustic vibration, and wherein said MEMS sensor weighs less than 30 mg and is less than 1 min$^3$ in dimension.

\* \* \* \* \*